US 8,252,035 B2
Aug. 28, 2012

(12) United States Patent
O'Connor et al.

(54) DEVICE DELIVERY SYSTEM WITH TWO STAGE WITHDRAWAL

(75) Inventors: Therese O'Connor, Athenry (IE); Michael Gilmore, Loughrea (IE); David Slattery, Kinvara (IE); Damian Kelly, Loughrea (IE)

(73) Assignee: Cappella, Inc., Auburndale, MA (US)

( * ) Notice: Subject to any disclaimer, the term of this patent is extended or adjusted under 35 U.S.C. 154(b) by 1213 days.

(21) Appl. No.: 11/832,002

(22) Filed: Aug. 1, 2007

(65) Prior Publication Data

US 2009/0036966 A1    Feb. 5, 2009

(51) Int. Cl.
*A61F 2/06* (2006.01)
(52) U.S. Cl. .......................................... 623/1.11
(58) Field of Classification Search ................. 623/1.12; 606/108, 198
See application file for complete search history.

(56) References Cited

U.S. PATENT DOCUMENTS

| | | | | |
|---|---|---|---|---|
| 5,549,635 A * | 8/1996 | Solar | ............................. | 623/1.12 |
| 5,702,418 A * | 12/1997 | Ravenscroft | .................. | 623/1.11 |
| 5,868,779 A * | 2/1999 | Ruiz | ............................... | 606/194 |
| 6,019,778 A * | 2/2000 | Wilson et al. | ................. | 606/198 |
| 6,113,608 A * | 9/2000 | Monroe et al. | ................ | 623/1.11 |
| 6,129,755 A * | 10/2000 | Mathis et al. | ................. | 623/1.15 |
| 6,273,895 B1 * | 8/2001 | Pinchuk et al. | ............... | 606/108 |
| 6,432,130 B1 * | 8/2002 | Hanson | .......................... | 623/1.11 |
| 6,443,971 B1 * | 9/2002 | Boylan et al. | ................. | 606/200 |
| 6,520,983 B1 * | 2/2003 | Colgan et al. | ................. | 623/1.11 |
| 6,629,992 B2 * | 10/2003 | Bigus et al. | ................... | 623/1.12 |
| 6,656,213 B2 | 12/2003 | Solem | | |
| 6,790,224 B2 * | 9/2004 | Gerberding | .................... | 623/1.12 |
| 6,859,986 B2 * | 3/2005 | Jackson et al. | ................... | 29/458 |
| 6,911,039 B2 * | 6/2005 | Shiu et al. | ..................... | 623/1.12 |
| 7,419,501 B2 * | 9/2008 | Chiu et al. | ..................... | 623/1.12 |
| 7,635,382 B2 * | 12/2009 | Pryor | ............................ | 623/1.11 |
| 2003/0199963 A1 * | 10/2003 | Tower et al. | .................. | 623/1.11 |
| 2004/0148000 A1 * | 7/2004 | Bilge | ............................ | 623/1.11 |
| 2005/0027305 A1 * | 2/2005 | Shiu et al. | ..................... | 606/108 |
| 2006/0015171 A1 * | 1/2006 | Armstrong | .................... | 623/1.12 |
| 2008/0140051 A1 * | 6/2008 | Bei et al. | ........................ | 604/509 |
| 2009/0048480 A1 * | 2/2009 | Klenk et al. | .................... | 600/37 |

FOREIGN PATENT DOCUMENTS

WO        0197715 A1    12/2001
WO        03039345 A2    5/2003

OTHER PUBLICATIONS

International Search Report for PCT Application No. PCT/US2008/071937, dated Jan. 29, 2009.

* cited by examiner

*Primary Examiner* — Gary Jackson
*Assistant Examiner* — Amy Shipley
(74) *Attorney, Agent, or Firm* — Rissman, Hendricks & Oliverio, LLP

(57) ABSTRACT

A medical device delivery system provides for a two-stage withdrawal of a deflated balloon portion of a catheter and the remains of a ruptured sheath. The deflated balloon portion is withdrawn from within an expanded medical device a predetermined distance before the remains of the ruptured sheath begins being removed from between the expanded device and a vessel wall. Initiating removal of the deflated balloon portion before the sheath reduces a total amount of drag that is exerted against a self-expanding medical device that has been deployed in a vessel.

13 Claims, 16 Drawing Sheets

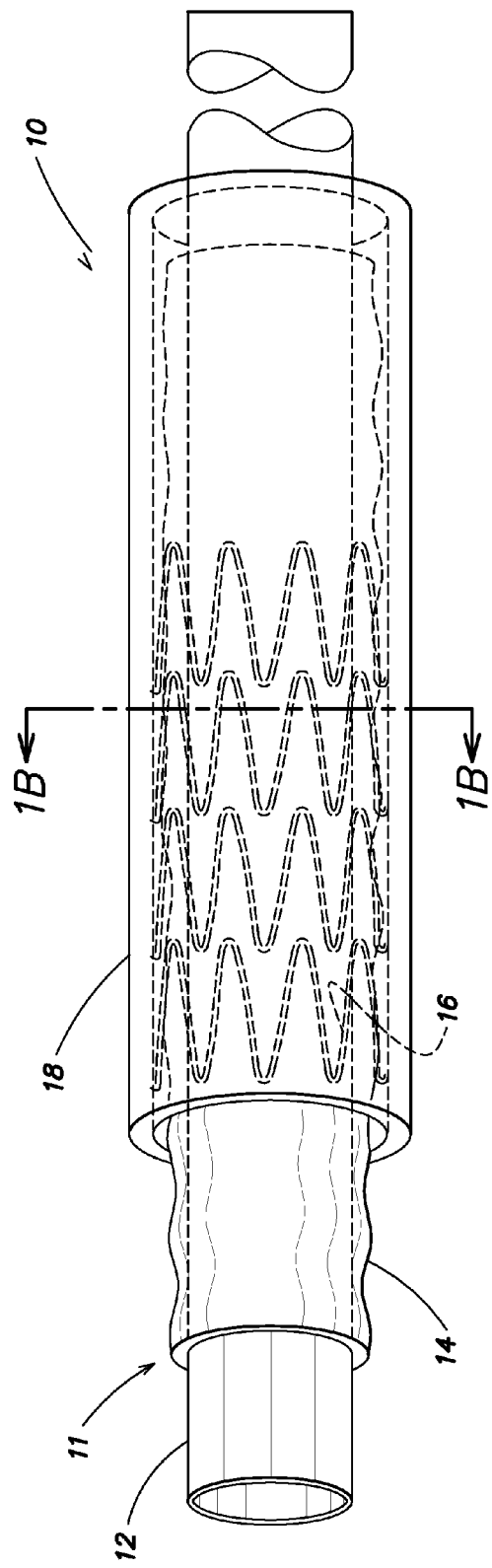
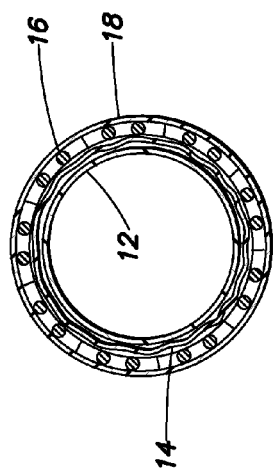
FIG. 1A
FIG. 1B

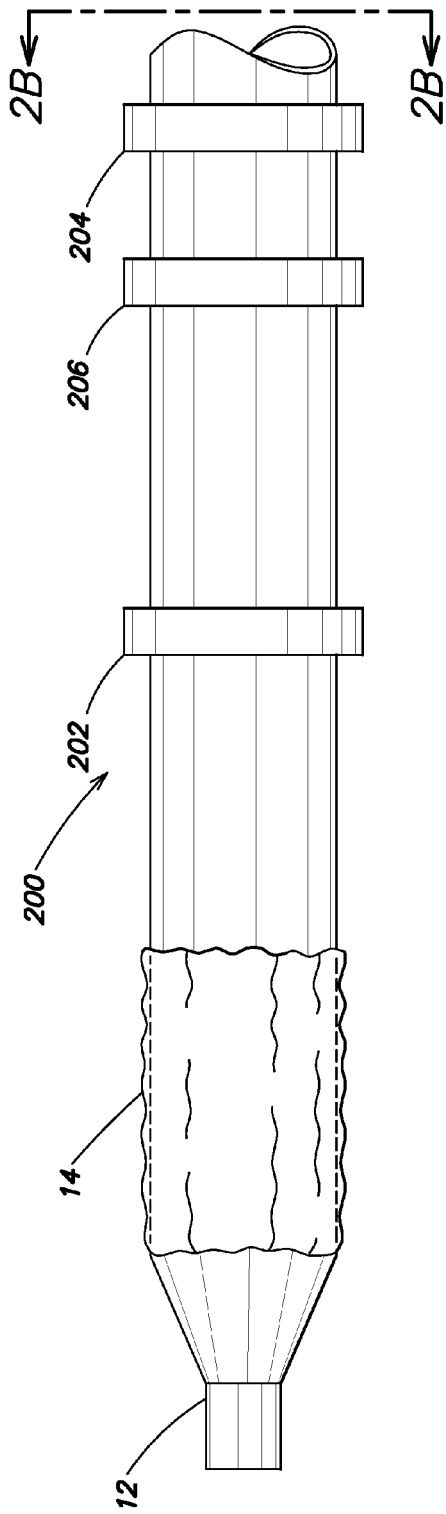
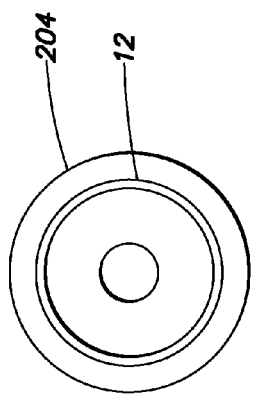
FIG. 2A
FIG. 2B

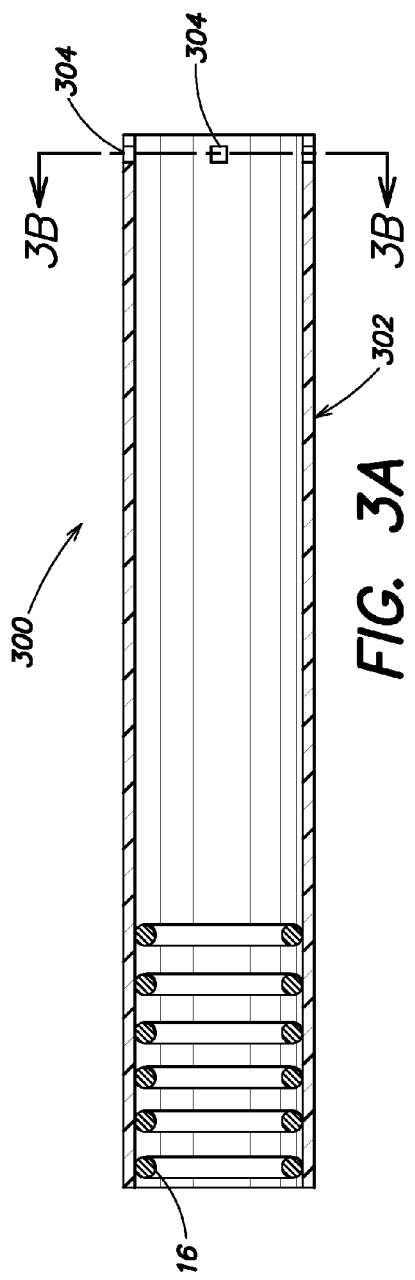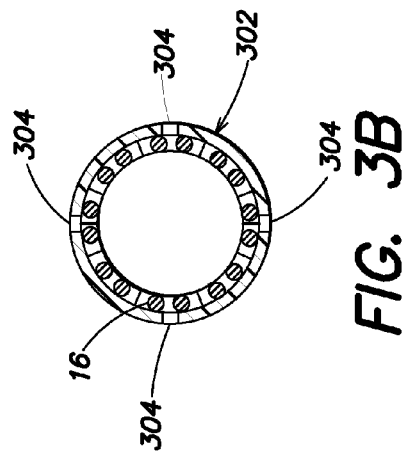
FIG. 3A
FIG. 3B

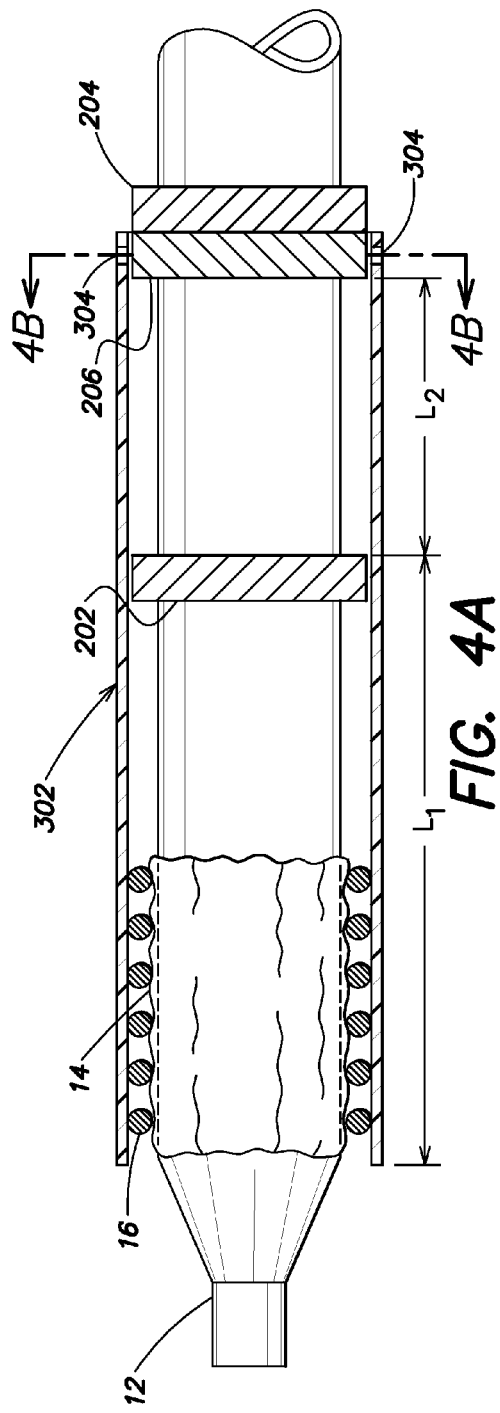
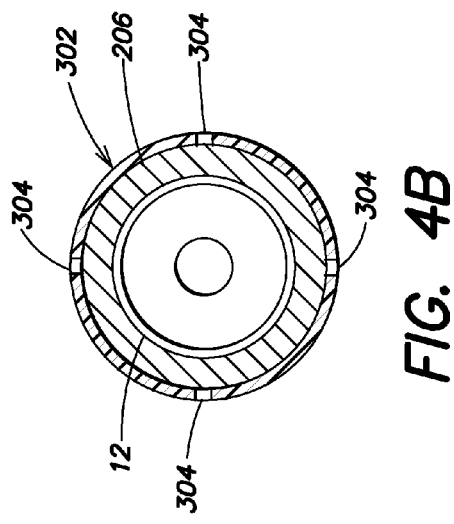
FIG. 4A
FIG. 4B

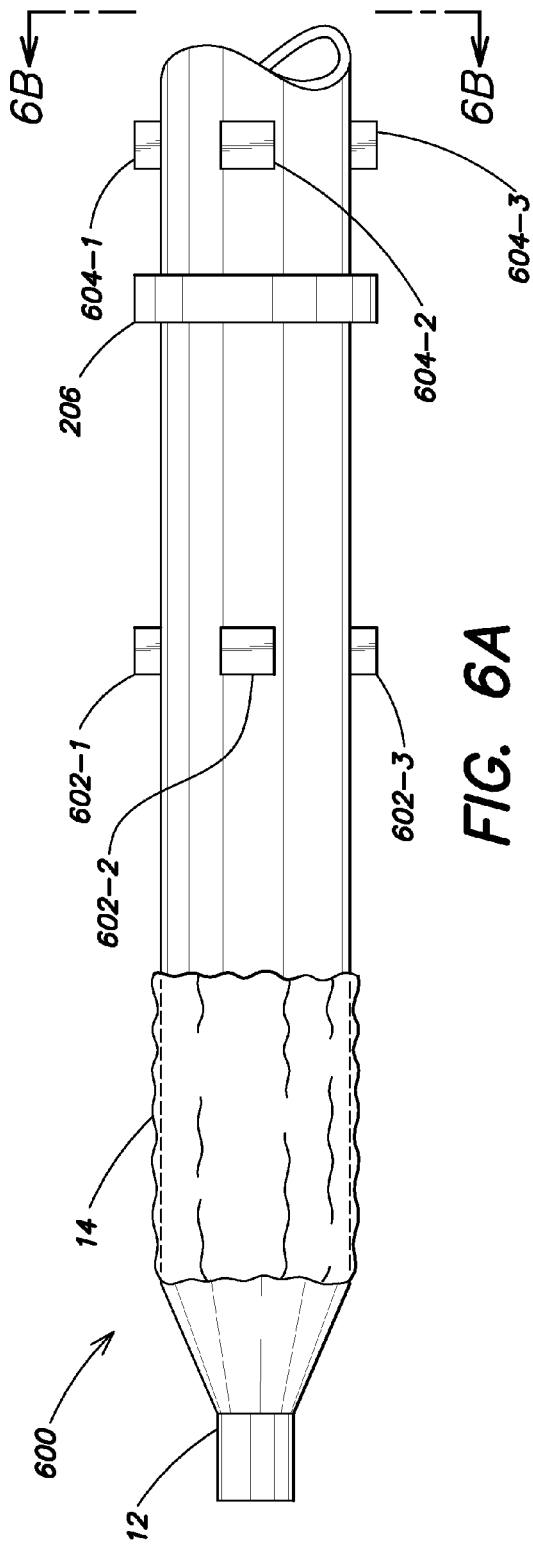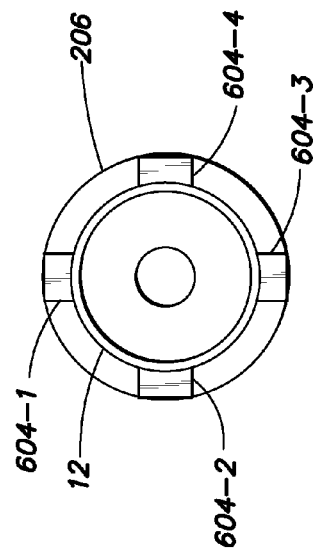
FIG. 6A
FIG. 6B

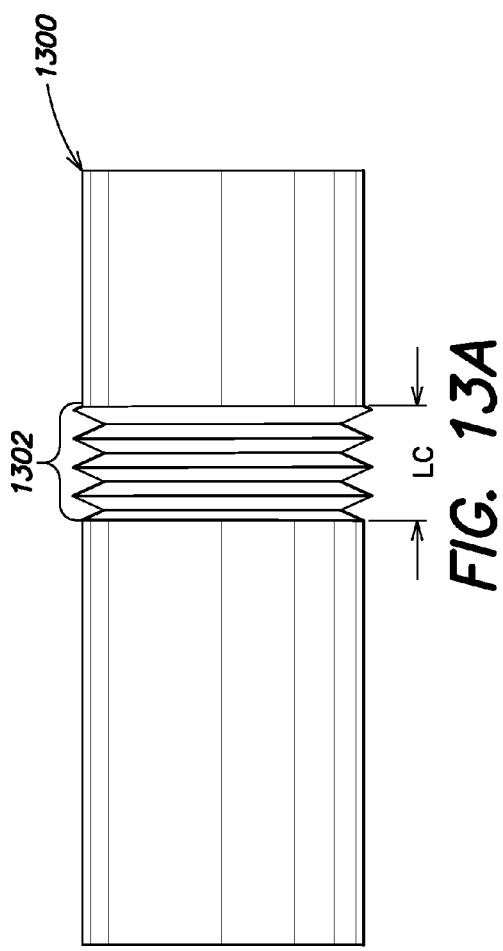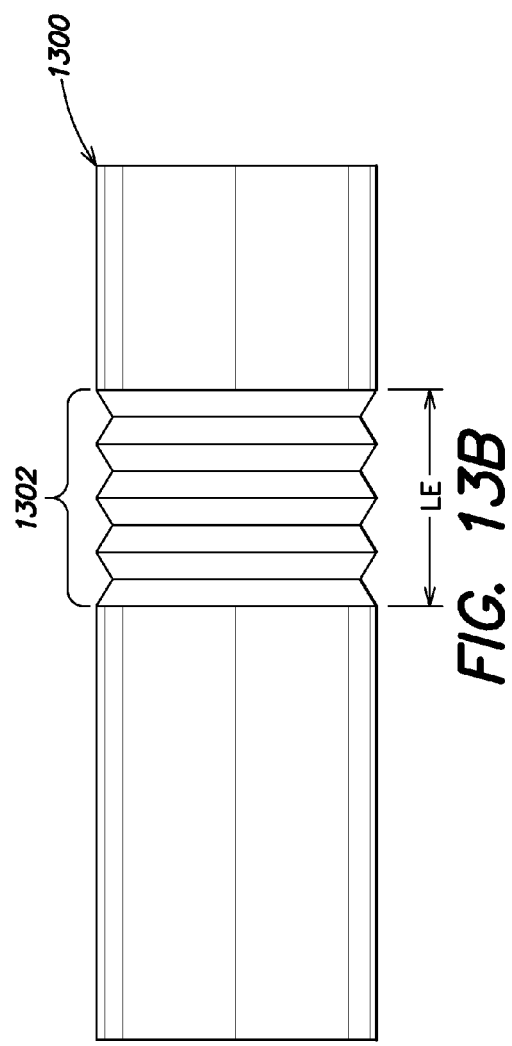

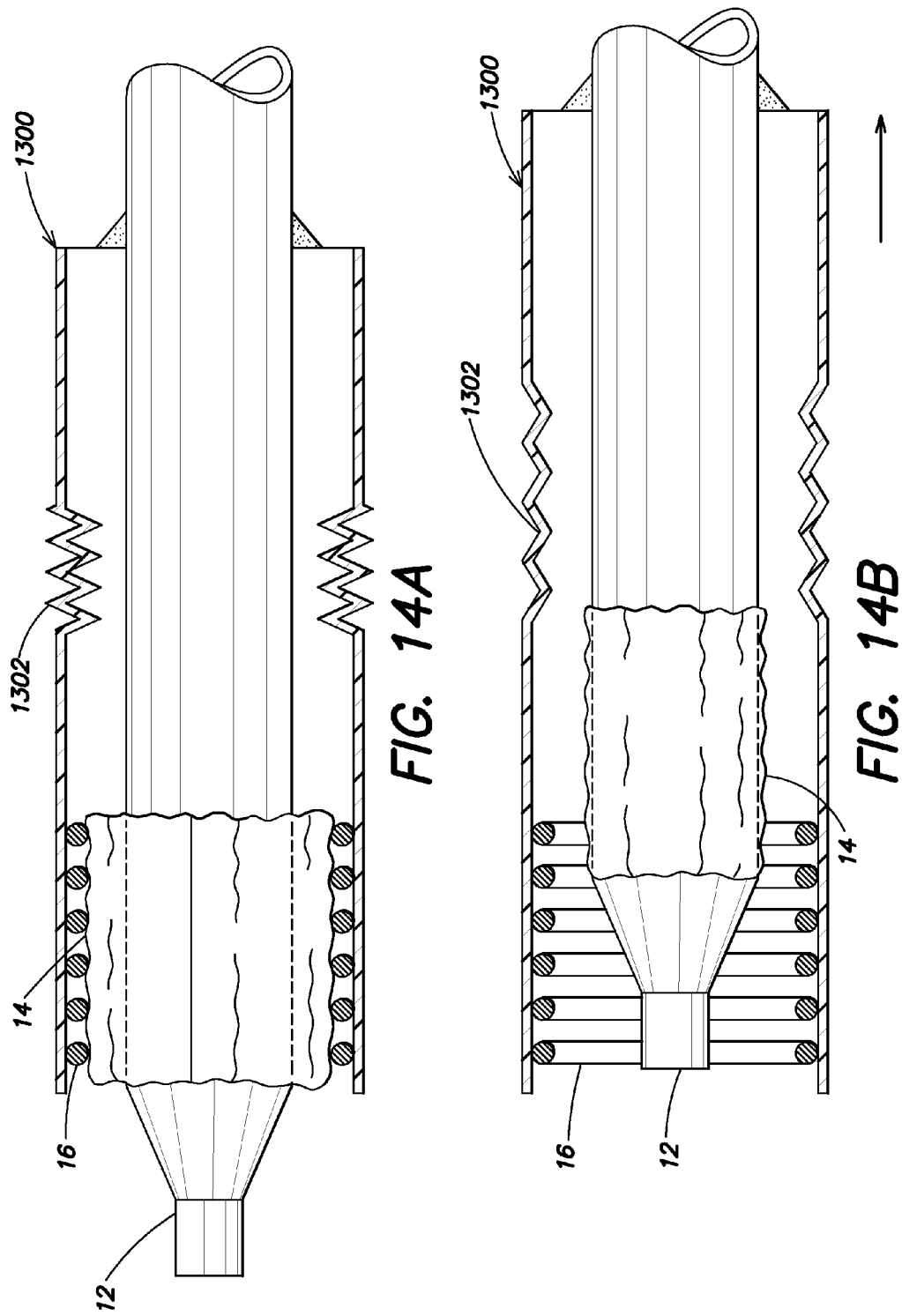

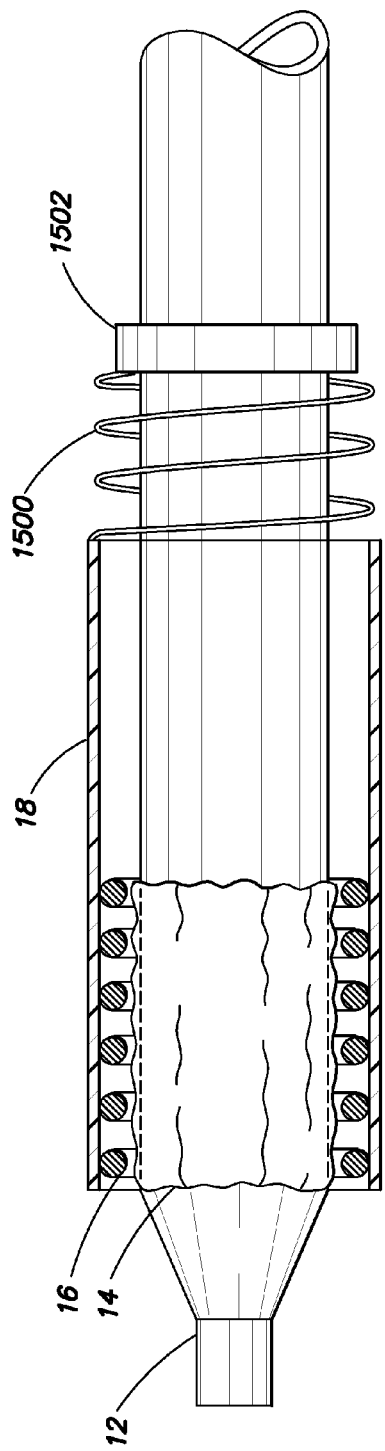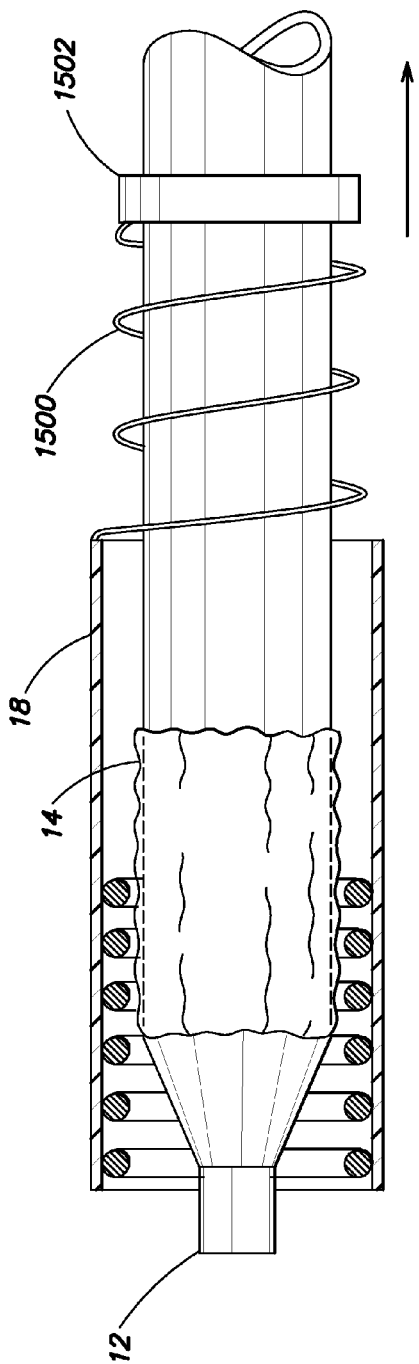

DEVICE DELIVERY SYSTEM WITH TWO STAGE WITHDRAWAL

RELATED APPLICATIONS

1. Field of the Invention

The present invention relates to a delivery system and method for deployment of a medical device, e.g., a self-expanding vascular device, in the vasculature of a patient. More particularly, a delivery system having a two-stage withdrawal mechanism is described.

2. Background of the Invention

As is known, treatment of vascular blockages due to any one of a number of conditions, such as arteriosclerosis, often comprises balloon dilatation and treatment of the inner vessel wall by placement of a stent. These stents are positioned to prevent restenosis of the vessel walls after the dilatation. Other devices, often referred to as drug eluting stents, are now being used to deliver medicine to the vessel wall to also help reduce the occurrence of restenosis.

These stents, i.e., tubular prostheses, typically fall into two general categories of construction. The first category of prosthesis is made from a material that is expandable upon application of a controlled force applied by, for example, a balloon portion of a dilatation catheter upon inflation. The expansion of the balloon causes the compressed prosthesis to expand to a larger diameter and then the prosthesis is left in place within the vessel at the target site. The second category of prosthesis is a self-expanding prosthesis formed from, for example, shape memory metals or super-elastic nickel-titanium (NiTi or Nitinol) alloys, that will automatically expand from a compressed or restrained state when the prosthesis is advanced out of a delivery catheter and into the blood vessel.

Some known prosthesis delivery systems for implanting self-expanding stents include an inner lumen upon which the compressed or collapsed prosthesis is mounted and an outer restraining sheath that is initially placed over the compressed prosthesis prior to deployment. When the prosthesis is to be deployed in the body vessel, the outer sheath is moved in relation to the inner lumen to "uncover" the compressed prosthesis, allowing the prosthesis to move to its expanded condition. Some delivery systems utilize a "push-pull" type technique in which the outer sheath is retracted while the inner lumen is pushed forward. Still other systems use an actuating wire that is attached to the outer sheath. When the actuating wire is pulled to retract the outer sheath and deploy the prosthesis, the inner lumen must remain stationary, preventing the prosthesis from moving axially within the body vessel.

There have been, however, problems associated with these delivery systems. For example, systems that rely on a "push-pull design" can experience movement of the collapsed prosthesis within the body vessel when the inner lumen is pushed forward. This movement can lead to inaccurate positioning and, in some instances, possible perforation of the vessel wall by a protruding end of the prosthesis. Systems that utilize an actuating wire design will tend to move to follow the radius of curvature when placed in curved anatomy of the patient. As the wire is actuated, however, tension in the delivery system can cause the system to straighten. As the system straightens, the position of the prosthesis changes because the length of the catheter no longer conforms to the curvature of the anatomy. This change of the geometry of the system within the anatomy can also lead to inaccurate prosthesis positioning.

Other delivery systems are known where a self-expanding stent is kept in its compressed state by a sheath positioned about the prosthesis. A balloon portion of the delivery catheter is provided to rupture the sheath and, therefore, release the prosthesis. As shown in U.S. Pat. No. 6,656,213, the stent may be provided around the balloon, with the sheath around the stent, that is, the balloon, stent, and sheath are co-axially positioned, such that expansion of the balloon helps to expand the self-expanding stent as well as rupture the sheath. In other embodiments, the balloon is outside the stent and the sheath is around both the balloon and the stent.

Once the balloon is inflated and the sheath is ruptured, the stent expands to its non-compressed state, or at least as much as it is able to depending upon the vessel in which it is placed. The ruptured sheath is now positioned between the expanded stent and the vessel wall. In some systems, the sheath is left in place, either permanently or to bio-degrade over time. In other systems, the sheath is withdrawn, usually when the delivery catheter is withdrawn from the vessel.

When withdrawing the ruptured sheath, both the deflated balloon and sheath move in unison and contact the deployed stent on its inside (contact with the deflated balloon) and on its outside (contact with the split or ruptured sheath). As a result the frictional force between stent-and-balloon and stent-and-sheath act simultaneously and this results in high retraction forces on the stent upon withdrawal of the catheter. This force can serve to reduce the ability of the stent to remain anchored at the target site.

There is, therefore, a need for a mechanism to reliably remove a ruptured sheath without disturbing the location of the delivered stent.

SUMMARY OF THE INVENTION

The present invention serves to address the problem presented by this simultaneous motion of sheath and balloon by allowing the sheath to remain in position whilst the deflated balloon is being withdrawn. This decouples the two components of frictional force that act on the deployed stent.

In one embodiment, there is provided a delivery system, comprising: a catheter having a distal end and a distal portion; a balloon portion disposed at the distal portion of the catheter; a first catheter stop disposed on the catheter at a first location a first distance from the distal end of the catheter; a second catheter stop disposed on the catheter a second distance from the distal end of the catheter, the second distance greater than the first distance; a sheath ring slidably disposed on the catheter between the first and second catheter stops; and a sheath disposed about the balloon portion, the sheath having a distal portion and a proximal portion, the proximal portion of the sheath coupled to the sheath ring.

In another embodiment, there is provided a delivery system, comprising: a catheter having a distal end and a distal portion; a balloon portion disposed on the distal portion of the catheter; a first catheter stop disposed on the catheter at a first location a first distance from the distal end of the catheter; a sheath ring slidably disposed on the catheter proximal to the first catheter stop; and a sheath disposed about the balloon portion and attached to the sheath ring.

The sheath may be of a predetermined length and may comprise a distal portion and a proximal portion, and the sheath ring may be attached to the sheath at the proximal portion of the sheath; and the first distance may be determined as a function of at least one of a length of the balloon portion and a length of the sheath.

In another embodiment, a system is provided, comprising: a catheter having a distal end and a distal portion; rupturing means disposed at the distal portion of the catheter; sliding means slidably coupled to the catheter; constraining means, disposed about the rupturing means, and coupled to the sliding means; and first stopping means, coupled to the catheter, for stopping movement of the sliding means.

In yet another embodiment of the present invention, a method of delivering a medical device to a predetermined location in a vessel of a body is provided, the method comprising: constraining the medical device in a compressed state on a delivery system; maneuvering the delivery system to position the constrained medical device substantially adjacent to the predetermined location; releasing the medical device from its constrained to deploy substantially at the predetermined location in the vessel; and withdrawing a first portion of the delivery system, followed by withdrawal of a second portion of the delivery system, by operation of a continuous movement of the delivery system.

In an alternate embodiment, a delivery system comprises: a catheter having a distal end and a distal portion; a balloon portion disposed on the distal portion of the catheter; and a sheath disposed about the balloon portion and coupled to the catheter at a location proximal to the balloon portion, wherein the sheath comprises a bellows portion having a compressed length and an expanded length.

In yet another embodiment, a delivery system comprises: a catheter having a distal end and a distal portion; a balloon portion disposed on the distal portion of the catheter; a sheath disposed about the balloon portion and having proximal and distal ends; and a tether coupling the proximal end of the sheath to a location on the catheter at a location proximal to the balloon portion.

A delivery system is provided, in one embodiment, the system comprising: a catheter having a distal end and a distal portion; a balloon portion disposed on the distal portion of the catheter; a sheath disposed about the balloon portion and the catheter; a plurality of sheath guides disposed on an interior surface of the sheath; and a catheter rail disposed on the catheter and engaged with at least one sheath guide of the plurality of sheath guides, the catheter rail comprising a predetermined pitch length.

BRIEF DESCRIPTION OF THE DRAWINGS

The above and further advantages of the present invention may be better understood by referring to the following description in conjunction with the accompanying drawings in which:

FIG. 1A is a view of a device delivery system;

FIG. 1B is a cross-sectional view of the device delivery system along line 1B-1B as shown in FIG. 1A;

FIGS. 2A and 2B are views of a portion of a device delivery system according to one embodiment of the present invention;

FIGS. 3A and 3B are views of a sheath assembly according to one embodiment of the present invention;

FIGS. 4A and 4B are views of the sheath assembly of FIG. 3A and the device delivery system of FIG. 2A according to one embodiment of the present invention;

FIGS. 6A and 6B are views of a portion of a device delivery system according to another embodiment of the present invention;

FIGS. 13A and 13B illustrate a sheath according to an alternate embodiment of the present invention;

FIGS. 14A and 14B illustrate the sheath of FIGS. 13A and 13B mounted on a delivery system;

FIGS. 15A and 15B illustrate a sheath coupled to a catheter according to an alternate embodiment of the present invention.

DETAILED DESCRIPTION

Figure 1C:
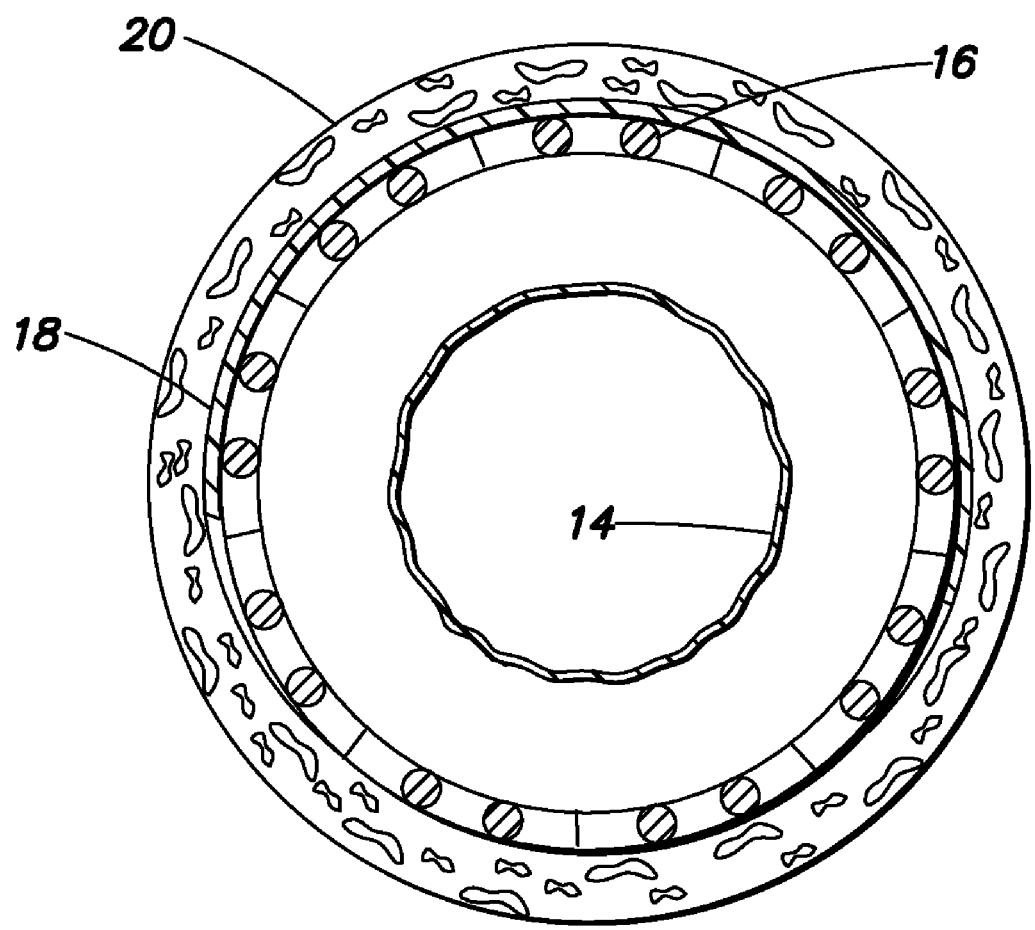
FIG. 1C is a representation of a cross-section of a vessel after rupturing of a sheath and expansion of a self-expanding medical device.

The simultaneous motion of the ruptured sheath and the catheter upon being withdrawn can interfere with the proper placement of the delivered medical device, i.e., the stent. The present invention serves to address the problem presented by this simultaneous motion of sheath and balloon by allowing the sheath to remain in position while the deflated balloon is being withdrawn. This mechanism decouples the two components of frictional force that can act on the deployed stent. The operation and configuration of embodiments of the present invention will be discussed in more detail below.

In general, a medical device delivery system, as shown in FIG. 1A, includes a delivery catheter 12 with a balloon portion 14 positioned at, or enclosing, a distal end 11 of the catheter 12. As is known, a lumen is provided to inflate the balloon 14 as necessary during the procedure to deliver a device 16, for example, a stent, that is placed at the distal end of the catheter 12 and around the balloon 14. As per the present discussion, the device 16 is a self expanding device and, therefore, a cylindrical sheath 18 is also disposed at the distal end 11 of the catheter 12 so as to enclose the device 16 and the balloon 14. The sheath 18 is attached to the catheter 12 at some point proximal to the distal end 11 of the catheter 12.

A cross-section of the system 10, along line 1B-1B, is presented in FIG. 1B. As shown, the sheath 18 surrounds the stent or device 16 and the balloon 14 positioned on the catheter 12.

As is known, the sheath 18 may be made from a material having a grain, or fibers, that can be longitudinally oriented, for example, PTFE. Other materials may be used for the sheath as understood by one of ordinary skill in the art. In general, the sheath 18, upon expansion of the balloon 14, will tear or rupture along a perforation or initial cut (not shown) in substantially a straight line following a longitudinal axis of the sheath 18 as defined, generally, by the catheter 12. The expansion of the balloon 14 causes the sheath 18 to rupture. Once the sheath 18 ruptures, the stent 16 expands and is released into the vessel.

The sheath 18 is made from a plastic material and, as above, is generally cylindrical. Once the sheath 18 ruptures, however, it is no longer a cylinder and has a form that covers less than all of the circumference of the now-expanded stent 16. Referring to FIG. 1C, a cross-section of the system 10 of FIG. 1A, the now-deflated balloon 14 is within the lumen of the expanded stent 16. As shown, the ruptured sheath 18 is trapped between a portion of the now-expanded stent 16 and a vessel wall 20. The ruptured sheath 18, however, is only trapped between the stent 16 and the vessel wall 20, for a portion, i.e., less than all, of the circumference of the now-expanded stent 16. When the catheter, and the now-deflated balloon, are withdrawn, that portion of the ruptured sheath 18 trapped between the stent 16 and the vessel wall 20 may pull on the deployed stent 16 and interfere with its proper placement. Further, depending upon the size and geometry of the vessel 20 in which the stent 16 is being placed, there also may be friction between the deflated balloon 14 and the stent 16.

A delivery system 200, in accordance with one embodiment of the present invention, will now be described with reference to FIGS. 2A and 2B. The system 200 includes a catheter 12 and balloon portion 14 as previously described. A distal catheter stop 202 is positioned on the catheter 12 a predetermined distance from the distal end 11 of the catheter 12. In one embodiment, the distal catheter stop 202 is a ring, for example, a radio-opaque (RO) platinum-iridium marker band as known to one of ordinary skill in the art. Alternatively, a gold RO marker band or heat-shrinkable tubing can be used. The determination of the predetermined distance from the distal end of the catheter will be described in more detail below.

The distal catheter stop 202 is attached to the catheter 12 in any one of a number of ways. These mechanisms for attaching the distal catheter stop 202 to the catheter 12 include, but are not limited to, gluing, riveting, swaging or implementing the catheter stop as an integrated part of the catheter 12.

In one embodiment, a proximal catheter stop 204 is also attached to the catheter 12 at a location proximal to the location of the distal catheter stop 202. Similarly to the distal catheter stop 202, the proximal catheter stop 204 may also be implemented as a marker band or ring. The distance between the distal catheter stop 202 and the proximal catheter stop 204 is a predetermined distance the details of which also will be discussed further below.

A sheath ring 206 is provided on the catheter at a location that is proximal to the distal catheter stop 202. The sheath ring 206 is not attached to the catheter 12 but is provided so as to slide along the outside of the catheter 12. In the embodiment that includes the proximal catheter stop 204 the sheath ring 206 is positioned so as to slide along the catheter 12 between the distal catheter stop 202 and the proximal catheter stop 204.

A cross-sectional view taken along the line 2B-2B, as shown in FIG. 2A, is presented in FIG. 2B.

As shown in FIG. 3A, a sheath assembly 300 comprises a sheath 302 including a self-expanding stent 16 being held by the sheath 302 in its compressed state. The sheath 302 and stent 16 may be made from materials that are known to one of ordinary skill in the art. The stent 16 is positioned substantially at a distal and of the sheath 302. The stent 16 is a self-expanding device that is compressed and loaded into the sheath 302. The sheath 302 loaded with the stent 16 is loaded over the balloon portion 14 as opposed to crimping the stent 16 directly onto the balloon 14. The stent 16 is deployed by inflating the balloon portion 14 which splits the sheath 302 and in turn allows the stent 16 to self-expand. In one embodiment, one or more openings or glue wicks 304 are provided about the circumference of the sheath 302 and are located at the proximal end, i.e., the end of the sheath 302 at which the stent 16 is not located. The glue wicks 304 are used to facilitate the connection of the sheath 302 to the sheath ring 206 as described below. A cross-sectional view taken along the line 3B-3B is provided in FIG. 3B.

The sheath 302 with the stent 16 disposed within it is placed over the distal end 11 of the catheter 12. The proximal end of the sheath 302 is slid over the balloon portion 14, past the distal catheter stop 202, and oriented with the sheath ring 206. The sheath 302 has a length such that the stent 16 is oriented adjacent to the balloon portion 14 and the proximal end of the sheath 302 extends proximally past the distal catheter stop 202. The characteristics of the sheath 302 maintain the position of the stent 16 about the balloon portion 14 of the catheter 12.

The one or more glue wicks 304 are aligned with the sheath ring 206 to facilitate the placement of glue that substantially permanently attaches the sheath 302 to the sheath ring 206. One of ordinary skill in the art will understand that other techniques or mechanisms for substantially permanently attaching the proximal end of the sheath 302 to the sheath ring 206 are possible. A cross-section of the system shown in FIG. 4A along the line 4B-4B is presented in FIG. 4B.

A first distance L1 from the distal end of the balloon portion 14, at which the proximal edge of the distal catheter stop 202 is placed, is a function of the length of the balloon portion 14 and the length of the stent 16. A second distance L2 represents the distance from the proximal edge of the distal catheter stop 202 to the distal edge of the sheath ring 206 as held in place by the sheath 302. The second distance L2 is a function of at least one of the length of the balloon portion 14 and the stent 16. The distance between the stops, and the location of the stops, is derived from the length of the stent and the length of the balloon portion. These two dimensions determine the length or distance that the catheter will be retracted before the ruptured sheath 302 begins being withdrawn. In addition, placing the proximal catheter stop 204 adjacent the sheath ring 206 prevents the sheath 302 from moving out of position while the catheter 12 is being distally advanced to the target site.

Figure 5A:
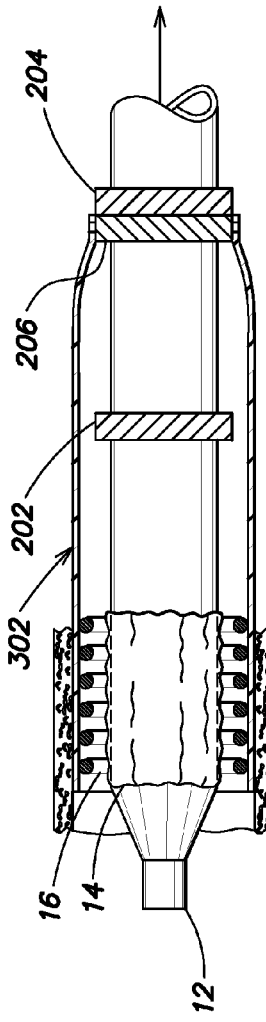
FIGS. 5A, 5B and 5C represent the withdrawal of the device delivery system in one implementation of the present invention.
Figure 5B:
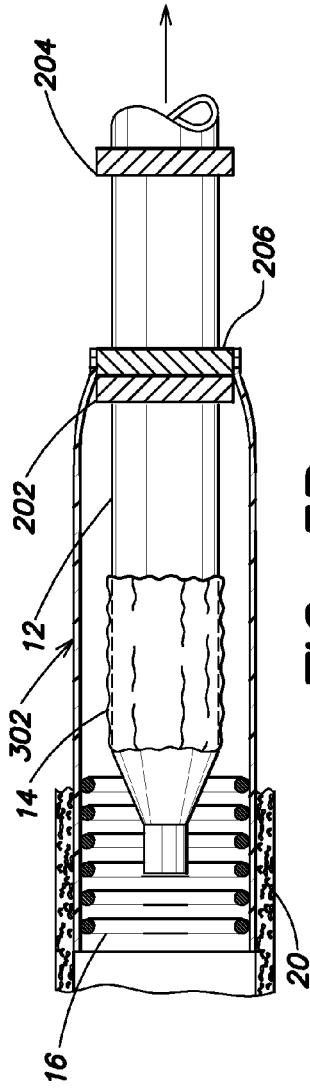
Figure 5C:
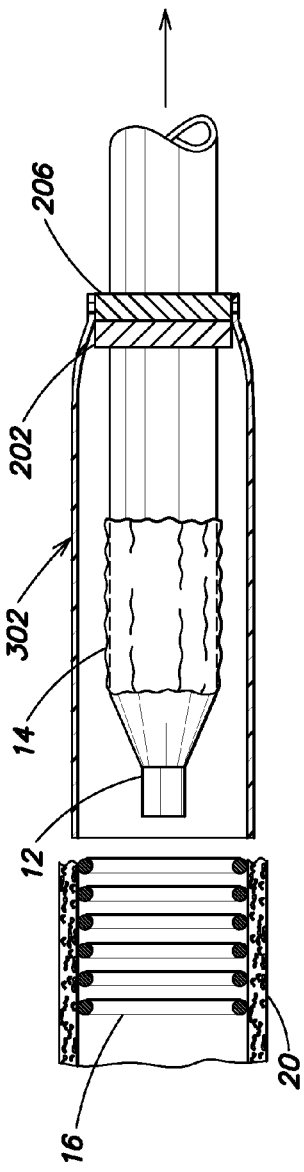

The operation of an embodiment of the present invention will now be described with reference to FIGS. 5A-5C. After the stent 16 is positioned at the desired location in the vessel 20, the balloon portion 14 is inflated sufficient to rupture the sheath 302. Once the sheath 302 is ruptured, the stent 16 expands to contact the vessel wall 20. The balloon portion 14 is then deflated to facilitate removal of the catheter 12. As shown in FIG. 5A, the sheath 302 is now located between some portion of the expanded stent 16 and the vessel wall 20.

As the catheter 12 is proximally withdrawn from the vessel 20, the sheath 302 will remain in position between the expanded stent 16 and the vessel 20. The catheter will move proximally and the sheath ring 206 will slide along the catheter 12, as shown in FIG. 5B.

Once the catheter 12 has been withdrawn a predetermined distance, in this case the distance L2, the distal catheter stop 202 will engage with the sheath ring 206. As the catheter 12 is further withdrawn, the sheath ring 206 will no longer slide along the catheter but instead will be moved proximally by the distal catheter stop 202. Movement of the sheath ring 206 will then pull the sheath 302 from between the expanded stent 16 and the vessel 20, as shown in FIG. 5C.

As a result of the positioning of the sheath ring 206 and the distal catheter stop 202, the balloon portion 14 of the catheter 12 will start to be removed from within the expanded stent 16 prior to the start of the removal of the sheath 302 from between the expanded stent 16 and the vessel 20. This operation occurs while the catheter 12 is being continuously withdrawn and does not require having to stop the withdrawal. Advantageously, by one continuous pulling operation of the catheter 12, the balloon and sheath are withdrawn in two steps or stages. This two-stage operation reduces the total amount of friction that may be applied to the expanded stent 16 if the balloon portion 14 and the sheath 302 trapped between the stent 16 and the vessel 20 were to be withdrawn at the same time.

In another embodiment of the present invention, a delivery system 600 includes a catheter 12 having a balloon portion 14. Instead of a distal catheter stop, however, a plurality of distal stop blocks 602 are attached about the circumference of the catheter 12. Further, in another embodiment, a plurality of proximal stop blocks 604 are provided about the circumference of the catheter 12. Similar to the system 200 shown in FIG. 2A, the sheath ring 206 is disposed to slide between the distal stop blocks 602 and the proximal stop blocks 604. A cross-sectional view taken along the line 6B-6B is presented in FIG. 6B. The distal stop blocks 602 and the proximal stop blocks 604 are shown as being symmetrically distributed about the circumference of the catheter 12, i.e., approximately 90° from one another. One of ordinary skill in the art would understand that these distal stop blocks 602 also could be unequally spaced about the circumference.

Figure 7:
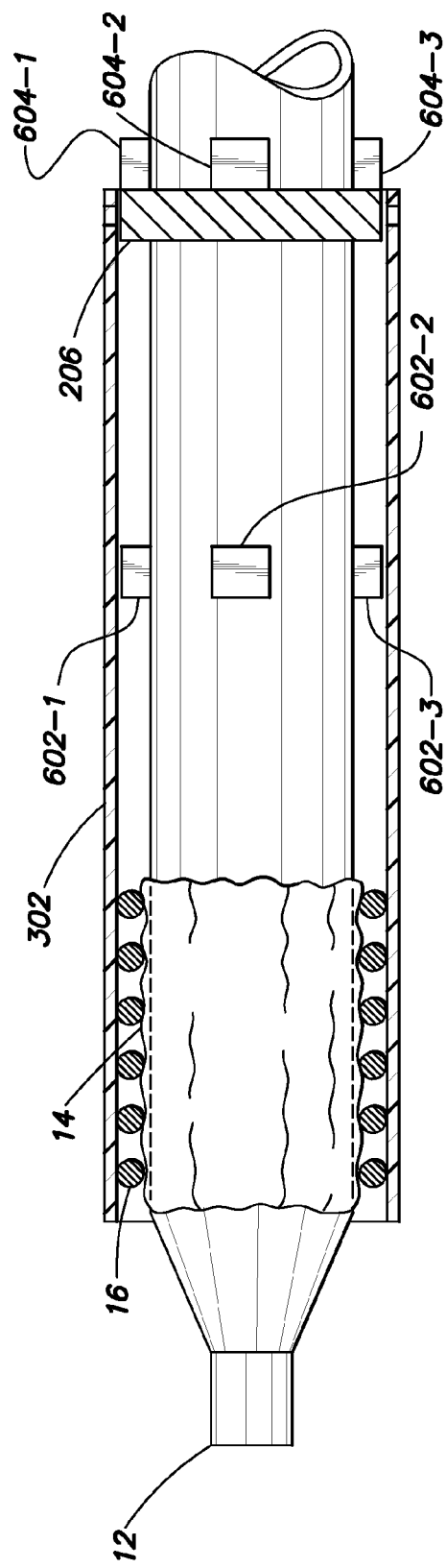
FIG. 7 is the device delivery system of FIG. 6A with the sheath assembly of FIG. 3A.

As shown in FIG. 7, the sheath 302 with the stent 16 is positioned about the distal portion of the catheter 12 and the sheath 302 is attached to the sheath ring 206. The operation of the system as shown in FIG. 7 is similar to that which has been described above.

Figure 8:
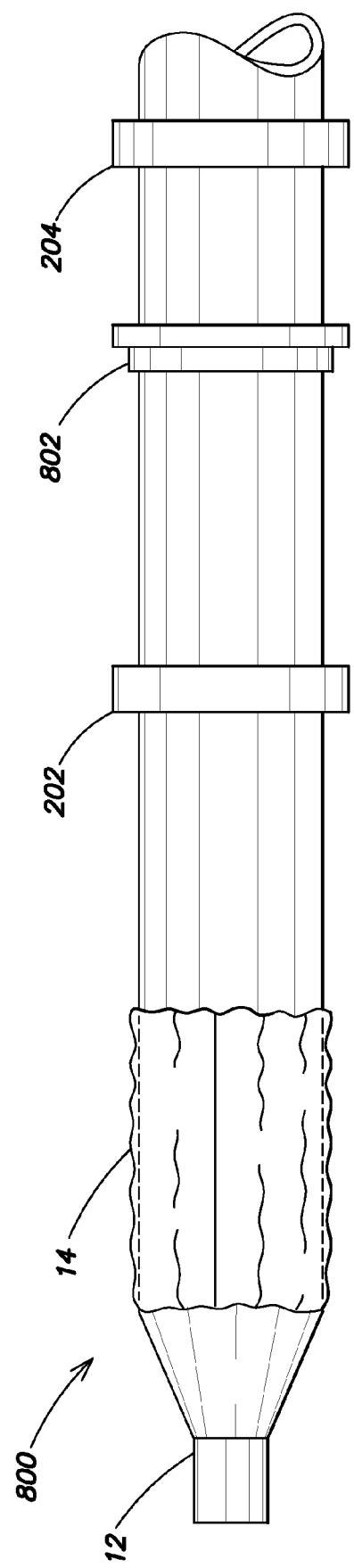
FIG. 8 is a view of a portion of a device delivery system according to one embodiment of the present invention.
Figure 9:
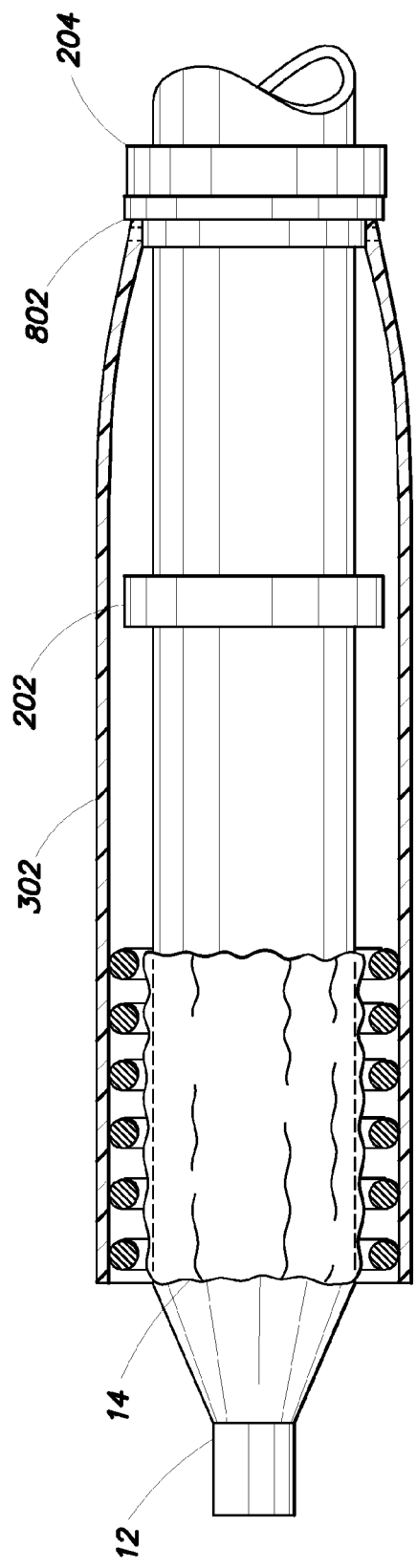
FIG. 9 is the device delivery system of FIG. 8 with the sheath assembly of FIG. 3A.

In yet another embodiment, as shown in FIG. 8, a system 800 includes the catheter 12 and the balloon portion 14 along with the distal catheter stop 202 and the proximal catheter stop 204. In this embodiment, a sheath cap ring 802 is provided. The sheath cap ring 802 is sized to fit into the proximal end of a sheath 302 as shown in FIG. 9.

Figure 10:
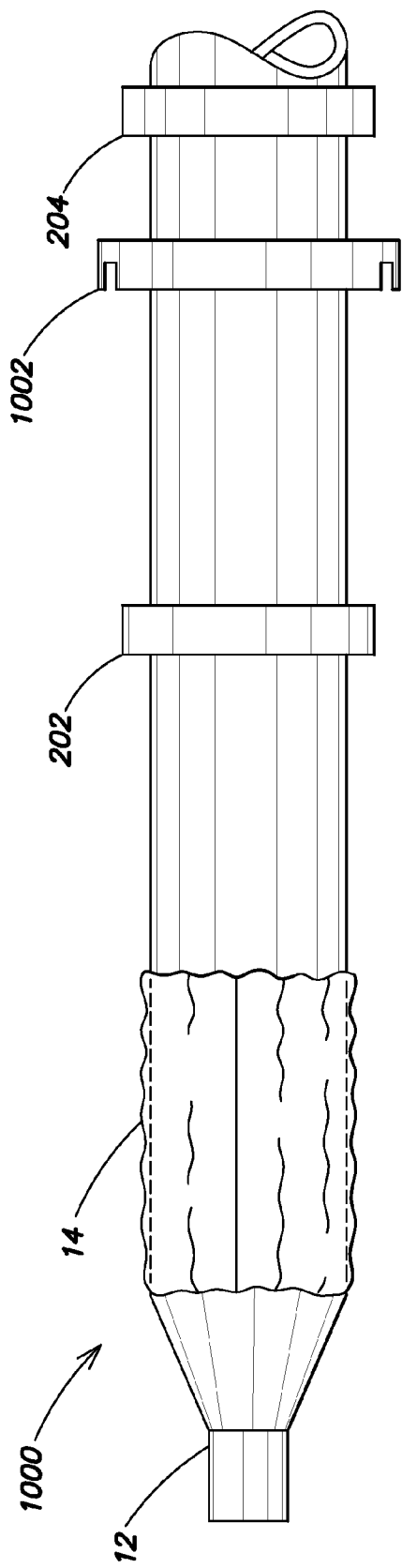
FIG. 10 is a view of a portion of a device delivery system according to one embodiment of the present invention.
Figure 11:
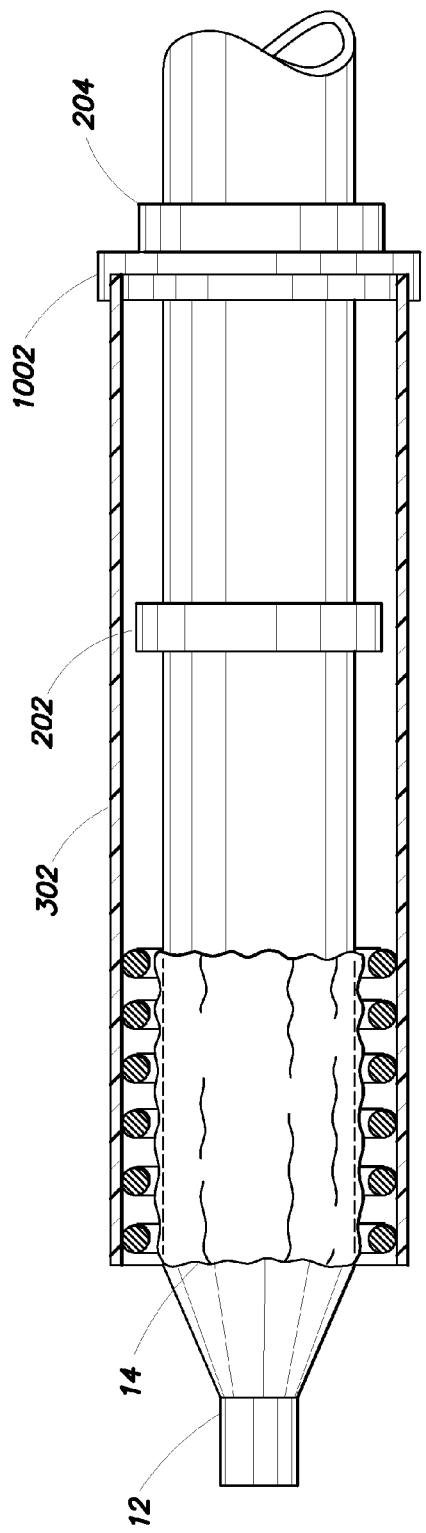
FIG. 11 is the device delivery system of FIG. 10 with the sheath assembly of FIG. 3A.

In yet another embodiment, as shown in FIG. 10, a system 1000 includes a catheter 12 and the balloon portion 14 along with the distal catheter stop 202 and the proximal catheter stop 204. A sheath cap 1002 is provided. The sheath cap 1002 is configured to receive the proximal end of a sheath 302 as shown in FIG. 11.

Figure 12:
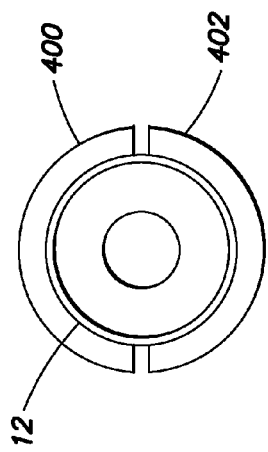
FIG. 12 is an alternate embodiment of a catheter stop and a sheath ring.

In the foregoing description, embodiments of the present invention described the distal catheter stop 202, the proximal catheter stop 204 and the sheath ring 206 as being marker bands. In one embodiment, the marker bands may be unitary or integral rings. Alternatively, the rings may be implemented in two parts as shown in FIG. 12. A first half-ring 400 and a second half-ring 402 can be used to implement either of the stops 202, 204 or the sheath ring 206. Further, in an alternate embodiment, one or the other of the half-rings 400, 402 may be used as one of the stops 202, 204. One of ordinary skill in the art would understand that the half-rings 400, 402 would have to be sized appropriately in order to contact the catheter 12, if implemented as either of the stops 202, 204 or to slide along the catheter 12, if implemented as the sheath ring 206. Further, one of ordinary skill in the art would also understand how the half-rings 400, 402 could either be connected to one another or to the catheter 12.

In an alternate embodiment of the present invention, a sheath 1300 includes a bellows portion 1302, as shown in FIGS. 13A and 13B. The bellows portion 1302 is similar to a "bendy-straw" used by young children, and some adults. The bellows portion 1302 has a compressed length LC and an expanded length LE.

The sheath 1300 is coupled, with the bellows portion 1302 in its compressed configuration, to a catheter 12 having a balloon portion 14 and a medical device 16, for example, a self-expanding stent, such that the stent 16 is held in place by the sheath 1300. The sheath 1300 has a predetermined length and is attached to the catheter 12 at a position a predetermined distance, in the proximal direction, from the distal end of the catheter 12, as shown in FIG. 14A.

In operation, similar to the embodiments described above, after the sheath 1300 is ruptured by the inflation of the balloon portion 14, the balloon portion 14 is deflated. The catheter 12 is then withdrawn proximally from the location in the vessel where the stent 16 is to be positioned. Similar to that which has been described above, some portion of the ruptured sheath 1300 is trapped between the expanded stent 16 and the blood vessel (not shown for clarity.) As the catheter 12 is withdrawn, FIG. 14B, the bellows portion 1302 expands to its expanded length LE. Once the bellows portion 1302 has reached its expanded length, the sheath 1300 will begin moving out from between the stent 16 and the vessel.

The expanded length LE is determined as a function of at least one of a length of the balloon portion 14 or the length of the medical device or stent 16. The expanded length LE provides this embodiment of the present invention with the ability to start removal of the balloon portion 14 from within the expanded device 16 prior to starting movement of the sheath 1300 from between the expanded stent 16 and the vessel.

The sheath 1300, in one embodiment, is glued directly to the outer surface of the catheter 12. Alternatively, the sheath 1300 may be attached to a sheath stop as described above. Of course, one of ordinary skill in the art would understand that there are a number of different mechanisms for attaching or coupling the sheath 1300 to the catheter 12.

In another embodiment of the present invention, a catheter 12 is provided with a balloon portion 14 about which a medical device or stent 16 is positioned. As shown in FIG. 15A, a sheath 18 is positioned about the device 16 and the balloon portion 14 so as to maintain the device 16 in its compressed state. A tether 1500 is wrapped around the catheter 12 and attaches a proximal portion of the sheath 18 to a tether anchor 1502.

In operation, FIG. 15B, after the sheath 18 is ruptured due to expansion of the balloon portion 14, similar to that which is described above, the catheter 12 is withdrawn. As above, some portion of the ruptured sheath 18 is trapped between the expanded device 16 and the vessel wall (not shown for clarity) and as the catheter 12 is withdrawn, the tether 1500 "spools out" allowing the deflated balloon portion 14 to move out proximally from within the expanded device 16 prior to movement of the sheath 18. Once the tether 1500 reaches its predetermined limit, the sheath 1800 will begin its withdrawal from between the stent 16 and the vessel.

The predetermined limit at which the tether 1500 stops spooling out is a function of one or more of a length of the stent 16, the balloon portion 14 and the sheath 18. Further, the location of the tether anchor 1502 is also chosen such that the balloon portion 14 moves a sufficient distance prior to the start of movement of the sheath 18 upon withdrawal.

Advantageously, the tether 1500 also serves to maintain the sheath 18 in position as the delivery system is being guided through the vessel anatomy to its destination. The compressed tether 1500 serves to prevent the sheath from being pushed proximally off of the distal end of the delivery system.

The tether 1500 may be made from any one of a number of appropriate materials, for example, a biocompatible thread or suture, a biocompatible metal, or a shape-memory metal such as Nitinol.

In one embodiment, the tether 1500 may be configured as a spring having a predetermined compressed length and a predetermined expanded length. The latter length would be chosen to represent the point at which the sheath would begin moving out from between the expanded stent 16 of the vessel wall as the catheter 12 is withdrawn.

The tether 1500 can be attached to the sheath 18 and the tether anchor 1502 by glue, mechanical fastener or any of a number of ways that are clear to one of ordinary skill in the art.

Figure 16A:
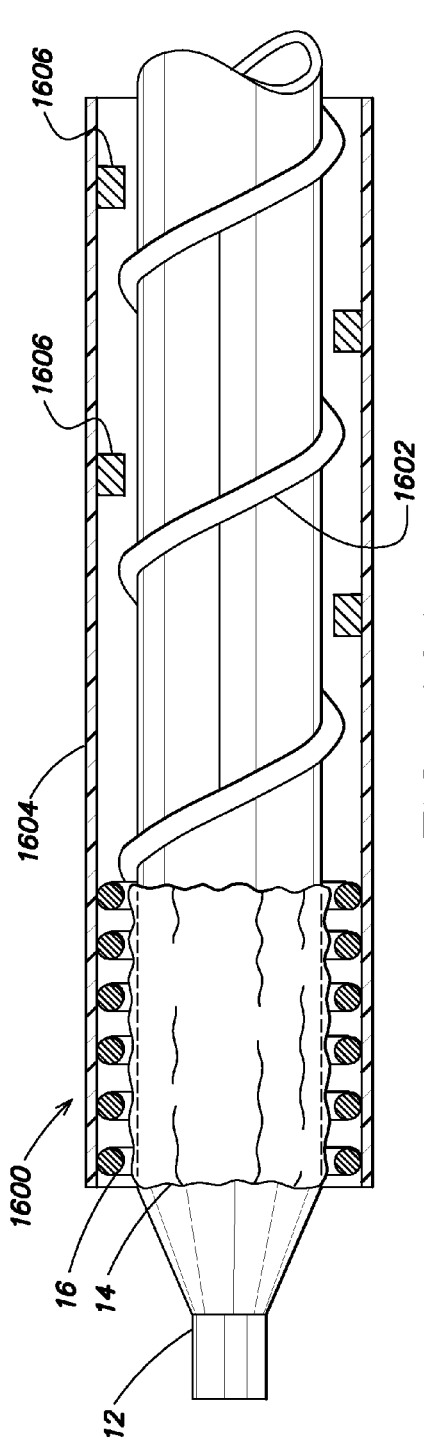
FIGS. 16A and 16B illustrate a delivery system according to an alternate embodiment of the present invention.

In another embodiment, a delivery system 1600 includes a catheter 12 that is provided with a mechanism that allows the catheter 12 to rotate as it is withdrawn from the vessel. Referring to FIG. 16A, a catheter 12 has a balloon portion 14 disposed at its distal end and a medical device 16 positioned about the balloon portion. A catheter rail 1602 is provided on a portion of the catheter 12 proximal to the balloon portion 14.

A sheath 1604 is positioned about the device 16 and balloon portion 14. The sheath 1604 includes a plurality of sheath guides 1606 disposed on an inner surface of the sheath 1604. The sheath guides 1606 are set apart from one another a longitudinal distance that is the same as a pitch of the catheter rail 1602. This distance is chosen as a function of at least a length of the balloon portion 14, a length of the stent 16 and a length of the sheath and 1604.

Figure 16B:
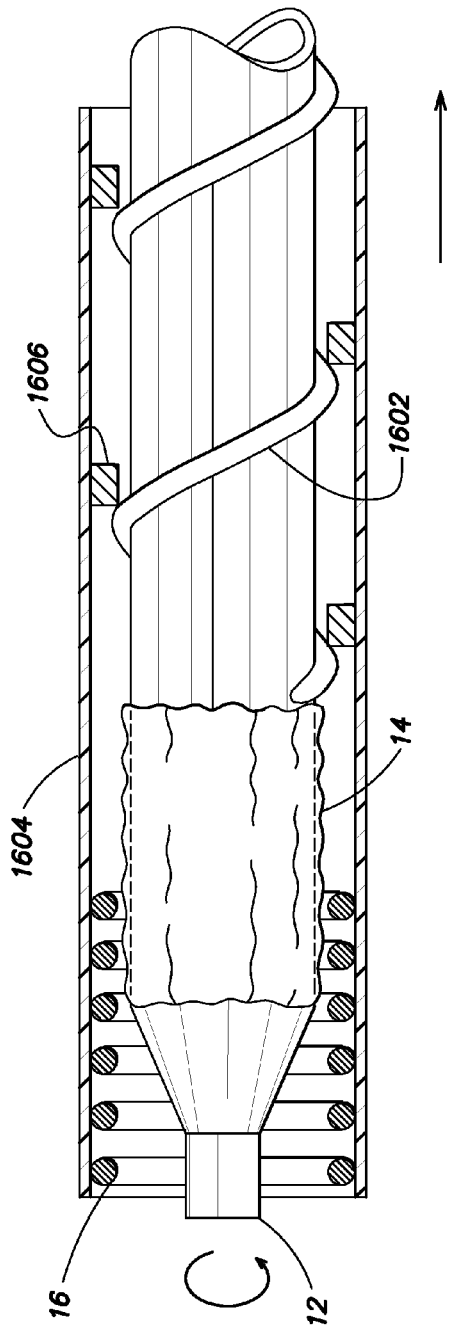

Similar to operation described above, once the sheath 1604 is ruptured, the catheter 12 is withdrawn from the vessel, FIG. 16B. As the catheter rail 1602 rides along the sheath guides 1606, the catheter 12 will turn as the sheath 1604 is held in place between the expanded stent 16 and the vessel wall (not shown for clarity.) Once the catheter rail 1602 has reached its spiral end, it will contact one or more of the sheath guides 1606 and the sheath and 1604 will begin its withdrawal from between the expanded stent 16 and the vessel wall.

Advantageously, by imparting a rotation to the catheter 12, the amount of drag that might occur, as the balloon portion 14 is withdrawn from the lumen of the expanded stent 16, is reduced.

The catheter rail 1602 may be provided as a separate component, for example, a spring or spiral assembly, wrapped about the catheter 12 and attached with, for example, glue. Alternatively, the catheter rail 1602 may be integral to the outer portion of the catheter 12, i.e., implemented as a polymer overmold thereon.

The sheath guide 1606, in one embodiment, is implemented as a spring or spiral situated inside the sheath 1604. The spring could be glued to the inside of the sheath. Alternatively, the sheath guides 1606, in another embodiment, may be implemented as indentations created on the inside of the sheath 1604 by a molding operation applied to the outside of the sheath 1604.

It is to be understood that the present invention is not limited in its application to the details of construction and the arrangement of the components set forth in the foregoing description or illustrated in the drawings. The invention is capable of other embodiments or of being practiced or carried out in various ways. Also, it is to be understood that the phraseology and terminology employed herein are for the purpose of description and should not be regarded as limiting.

It is further appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although various exemplary embodiments of the present invention have been disclosed, it will be apparent to those skilled in the art that changes and modifications can be made that will achieve some of the advantages of the invention without departing from the spirit and scope of the invention. It will be apparent to those reasonably skilled in the art that other components performing the same functions may be suitably substituted.

What is claimed is:

1. A delivery system, comprising: a catheter having a distal end and distal portion;
   a balloon portion disposed on the distal portion of the catheter;
   a sheath disposed about the balloon portion;
   a first catheter stop disposed on the catheter at a first location a first distance from the distal end of the catheter; and
   a sheath ring fixedly coupled with the sheath and slidable on the catheter proximal to the first catheter stop, the first catheter stop being configured such that as the catheter is moved proximally relative to the sheath, the first catheter stop engages the sheath ring and moves the sheath proximally.

2. The delivery system of claim 1, wherein the sheath is of a predetermined length and comprises a distal portion and a proximal portion, and wherein:
   the sheath ring is attached to the sheath at the proximal portion of the sheath; and
   the first distance is determined as a function of at least one of a length of the balloon portion and a length of the sheath.

3. The delivery system of claim 1, further comprising:
   a second catheter stop disposed on the catheter at a second distance from the distal end of the catheter, the second distance greater than the first distance.

4. The delivery system of claim 1, further comprising:
   a medical device disposed about the balloon portion and restrained by the sheath.

5. The delivery system of claim 4, wherein the medical device is a self-expanding stent.

6. The delivery system of claim 4, wherein a length of the sheath is determined as a function of at least one of:
   a length of the balloon portion; and
   a length of the medical device.

7. The delivery system of claim 4, wherein:
   a distance which the proximal portion of the sheath extends beyond the location of the first catheter stop is determined as a function of at least one of:
   a length of the balloon portion; and
   a length of the medical device.

8. The delivery system of claim 7, further comprising:
   a second catheter stop disposed on the catheter at a second location a second distance from the distal end of the catheter,
   wherein the second distance is greater than the first distance.

9. The delivery system of claim 8, wherein:
   a difference between the first and second distances is determined as a function of at least one of:
   a length of the balloon portion; and
   a length of the medical device.

10. The delivery system of claim 8, wherein:
    the second location is substantially adjacent the sheath ring as held in place by the proximal portion of the sheath.

11. A method of delivering a medical device to a predetermined location in a vessel of a body, the method comprising:
    constraining the medical device in a compressed state on a catheter with a sheath;
    maneuvering a delivery system to position the constrained medical device substantially adjacent to the predetermined location;

releasing the medical device from its compressed state to deploy substantially at the predetermined location in the vessel; and withdrawing the catheter proximally and sliding the catheter relative to the sheath, and continuing withdrawal of the catheter to engage a member fixedly coupled to the sheath so as to urge the sheath proximally together with the catheter.

12. The method of claim 11, wherein the medical device is a self-expanding stent.

13. The method of claim 12,
wherein releasing the stent from the sheath comprises:
inflating a balloon portion of the catheter to rupture the sheath.

* * * * *